(12) United States Patent
Bakker et al.

(10) Patent No.: US 12,343,536 B2
(45) Date of Patent: Jul. 1, 2025

(54) NEUROSTIMULATION SYSTEM

(71) Applicant: INBRAIN Neuroelectronics S.L., Barcelona (ES)

(72) Inventors: Bert Bakker, Wijk en Aalburg (NL); Michel Decre, Eindhoven (NL); Jose Antonio Garrido Ariza, Barcelona (ES)

(73) Assignee: INBRAIN NEUROELECTRONICS S.L., Barcelona (ES)

( * ) Notice: Subject to any disclaimer, the term of this patent is extended or adjusted under 35 U.S.C. 154(b) by 0 days.

(21) Appl. No.: 17/827,549

(22) Filed: May 27, 2022

(65) Prior Publication Data

US 2022/0387791 A1 Dec. 8, 2022

(30) Foreign Application Priority Data

Jun. 3, 2021 (EP) .................................... 21382494

(51) Int. Cl.
*A61N 1/36* (2006.01)
*A61N 1/05* (2006.01)
(Continued)

(52) U.S. Cl.
CPC ......... *A61N 1/3606* (2013.01); *A61N 1/0531* (2013.01); *A61N 1/0534* (2013.01);
(Continued)

(58) Field of Classification Search
CPC .. A61N 1/3606; A61N 1/0531; A61N 1/0534; A61N 1/36146; A61N 1/37223;
(Continued)

(56) References Cited

U.S. PATENT DOCUMENTS 8,423,155 B1 * 4/2013 Jaax ..................... A61N 1/0526
607/45
10,342,429 B2 * 7/2019 Chin .................. A61N 1/37205
(Continued)

FOREIGN PATENT DOCUMENTS

WO 2015191628 A1 11/2015

OTHER PUBLICATIONS

Apollo, N. V., Maturana, M. I., Tong, W., Nayagam, D. A. X., Shivdasani, M. N., Foroughi, J., Wallace, G. G., Prawer, S., Ibbotson, M. R., & Garrett, D. J. (2015). Soft, flexible freestanding neural stimulation and recording electrodes fabricated from reduced graphene oxide. Advanced Functional Materia.*
(Continued)

*Primary Examiner* — Paula J Stice
(74) *Attorney, Agent, or Firm* — McCoy Russell LLP

(57) ABSTRACT

The present disclosure relates to a neurostimulation system, in particular for Cortical and/or Deep Brain Stimulation, comprising:
at least one implant unit comprising:
at least one first antenna, and
at least one lead having at least one electrode array with at least one electrode; and
at least one wearable device comprising at least one second antenna,
wherein the at least one wearable device is configured to wirelessly control and wirelessly communicate with the at least one implant unit, and wherein the at least one electrode is made of reduced graphene oxide, such as hydrothermally reduced graphene oxide.

22 Claims, 3 Drawing Sheets

(51) Int. Cl.
  *A61N 1/372* (2006.01)
  *A61N 1/378* (2006.01)
(52) U.S. Cl.
  CPC ..... *A61N 1/36146* (2013.01); *A61N 1/37223* (2013.01); *A61N 1/3787* (2013.01)
(58) Field of Classification Search
  CPC .............. A61N 1/3787; A61N 1/37229; A61N 1/37235
  See application file for complete search history.

(56) References Cited

U.S. PATENT DOCUMENTS

| | | | |
|---|---|---|---|
| 2001/0023360 A1* | 9/2001 | Nelson | G16H 40/67 607/60 |
| 2002/0076071 A1* | 6/2002 | Single | H04R 25/606 381/323 |
| 2011/0087306 A1* | 4/2011 | Goossen | A61N 1/3718 607/60 |
| 2013/0165996 A1* | 6/2013 | Meadows | A61N 1/3605 607/116 |
| 2014/0058506 A1* | 2/2014 | Tai | A61N 1/3787 623/4.1 |
| 2016/0121129 A1* | 5/2016 | Persson | A61N 1/37288 607/32 |
| 2016/0274752 A1* | 9/2016 | Zhu | G06F 3/017 |
| 2017/0189699 A1* | 7/2017 | Dellamano | A61N 1/36071 |
| 2018/0304086 A1* | 10/2018 | Shellhammer | A61B 5/6847 |
| 2019/0054295 A1 | 2/2019 | Pannu et al. | |
| 2020/0086129 A1* | 3/2020 | Min | A61N 1/3756 |
| 2020/0314565 A1* | 10/2020 | Sigwanz | H04R 25/40 |
| 2021/0093873 A1* | 4/2021 | Chin | A61N 1/37 |
| 2021/0106833 A1* | 4/2021 | von Arx | A61N 1/37288 |
| 2022/0144644 A1 | 5/2022 | Garrido Ariza et al. | |

OTHER PUBLICATIONS

Apollo, Nicholas V., et al. "Soft, Flexible Freestanding Neural Stimulation and Recording Electrodes Fabricated from Reduced Graphene Oxide." Advanced Functional Materials, vol. 25, No. 23, May 4, 2015, pp. 3551-3559, https://doi.org/10.1002/adfm.201500110 (Year: 2015).*

Huang, Hsin-Hui, et al. "Structural Evolution of Hydrothermally Derived Reduced Graphene Oxide." Scientific Reports, vol. 8, No. 1, May 1, 2018, https://doi.org/10.1038/s41598-018-25194-1 (Year: 2018).*

Apollo, N. et al., "Soft, Flexible Freestanding Neural Stimulation and Recording Electrodes Fabricated from Reduced Graphene Oxide," Material Views, vol. 25, No. 23, May 4, 2015, 9 pages.

Bramini, M. et al., "Interfacing Graphene-Based Materials with Neural Cells," Frontiers in Systems Neuroscience, vol. 12, No. 12, Apr. 11, 2018, 42 pages.

European Patent Office, Extended European Search Report Issued in Application No. 21382494.9, Nov. 30, 2021, Germany, 7 pages.

European Patent Office, Office Action Issued in Application No. 21382494.9, Jul. 28, 2023, Germany, 4 pages.

* cited by examiner

NEUROSTIMULATION SYSTEM

CROSS-REFERENCE TO RELATED APPLICATION

The present application claims priority to European Patent Application No. 21382494.9 filed on Jun. 3, 2021. The entire contents of the above-listed application is hereby incorporated by reference for all purposes.

TECHNICAL FIELD

The present disclosure relates to a neuromodulation system, in particular a subgaleal implant system for Cortical and/or Deep Brain Stimulation and/or Modulation, and to a method for neuromodulation.

BACKGROUND

In practice, it is known that Cortical and/or Deep Brain Stimulation and/or Modulation is a method for the diagnosis and therapy of neurodegenerative diseases such as inter alia the Parkinson's disease, epilepsy, and chronic pain. In this respect, electrical stimulation by means of leads which were implanted into brain areas or regions like the subthalamic nucleus and/or the globus pallidus internus can e.g. alleviate the tremor symptoms of a patient suffering from a drug-resistant Parkinson's disease. Further, the signals from a brain region or area at which the leads were implanted can be recorded and the state of the brain tissue can be determined using impedance measurements.

SUMMARY

In this relation, neuroprosthetic devices are powerful tools to monitor, prevent and treat neural diseases, disorders and conditions by interfacing electrically with the nervous system. They are capable of recording and stimulating electrically neural activity once implanted in the nervous tissue. Currently, most neuroprosthetic technologies base their interface with the neural tissue on electrodes.

For stimulation, the electrodes are usually controlled by an Implantable Pulse Generator (IPG).

A substantial part of the volume and size of conventional IPGs for brain therapy implants is taken by charge-balancing blocking-capacitors, connectors, a primary or rechargeable battery, and the hermetic—typically metal—enclosure.

Besides, conventional IPGs being implanted, puts severe constraints on engineering options, technology upgrades, and the bulk of surgical replacement in case of failure or obsolescence of the installed technology.

This creates a steadily increasing gap between, on the one hand, the high-tech devices like smartphones, tablets, laptops, etc. used daily in the hands of billions of people, and being inter alia replaced each time they change provider or subscription, and, on the other hand, electronic implantable medical devices that stay implanted for ten or more years without hardware improvement, and are designed with conservative technology.

One exception to this are cochlear implants. These implants use an addressable array of typically 22 electrodes (vs. typically 4 to 8 segments for Deep Brain Stimulation or 8 to 16 paddle electrodes for Spinal Cord Stimulation) for real-time sound processing and cochlear nerve stimulation. One aspect of cochlear systems is that the sound recording and processing, and the stimulation electronics are carried behind the ears of the patient. However, the high band width of sound processing and permanent real-time cochlear stimulation requires excellent wireless coupling between the wearable electronic behind-the-ear enclosure and the implanted secondary antenna of the implanted lead comprising the electrodes. This is normally achieved by a cable connection from the behind-the-ear device to the antenna, which is centered and maintained in place by a magnet implant attached in the skull bone; a solution that is burdensome, bulky, and cosmetically less and less accepted.

While there have been some proposals to replace the chest-implanted IPGs and lead cables running inside the neck with a cranial implant, such implants complicate surgery, involve intricate cranial bone surgery that weakens the bone in the implant region, increases infection risk both directly after surgery and in the long term, as well as skin erosion, while not resolving the issues of technology obsolescence, and replacement, which implies another head surgery, being more cumbersome and tricky, compared to chest-implanted.

From US 2019/0054295 A1 it is known that a modular system for deep brain stimulation (DBS) and electrocorticography (ECoG) may have an implantable neuromodulator for generating electrical stimulation signals adapted to be applied to a desired region of a brain via an attached electrode array. An aggregator module may be used for collecting and aggregating electrical signals and transmitting the electrical signals to the neuromodulator. Further, a control module may be used which is in communication with the aggregator module for controlling generation of the electrical signals and transmitting the electrical signals to the aggregator. In other words, an aggregator connecting several electrode arrays, and sharing the signals and stimulation as well as some computing with an external or wearable device is provided. However, the aggregator contains implantable parts. This once more causes the proposed solution to cross the skin, creating an infection port, and requiring permanent care.

Therefore, it is an object of the present disclosure to develop a neuromodulation system providing the requirements of the aforementioned kind, in particular in such a way that that the extent and frequency of the related medical surgery is reduced.

According to the present disclosure, a neuromodulation system, in particular for Cortical and/or Deep Brain Stimulation and/or Modulation, is provided which comprises:
- at least one implant unit comprising:
  - at least one first antenna, and
  - at least one lead having at least one electrode array with at least one electrode; and
- at least one wearable device comprising at least one second antenna,
- wherein the at least one wearable device is configured to wirelessly control and wirelessly communicate with the at least one implant unit, and wherein the at least one electrode is made of reduced graphene oxide, such as hydrothermally reduced graphene oxide.

The basic idea of the present disclosure is to replace standard chest-implanted brain stimulation IPGs with a wearable device, in particular a behind-the-ear device, containing, for example, control electronics, a rechargeable power source and an antenna or transducer for a power, data and/or control link. As a corresponding counterpart, an implanted unit comprising inter alia another antenna is located under the scalp behind the ear. The implanted unit may additionally include at least one capacitor and/or an (electronic) module and/or an element to receive and/or smoothen variations of transferred power caused by relative motion of the wearable device's antenna with respect to the antenna of the implanted unit. Furthermore, although brain stimulation needs to be continuous and smooth not to cause patient discomfort or interruption of therapy, the band width involved in most therapeutic brain stimulation is not very high, particularly once the therapeutic protocol has been consolidated. Signal processing and therapy adjustment can therefore be slightly delayed, or performed in a slow manner. It is therefore all the more important that the smoothening effect of the capacitor or module allows a corresponding system to compensate for variations of wireless coupling between the antennas, analogous—although not strictly identical—to the effect of the numerical aperture in compact-disk and blue-ray disk, which reduces the sensitivity of the optical disk system to dust on the disk surface or other slight optical variations. Moreover, by using a wearable or behind-the-ear device having an integrated antenna, with a power transfer buffer 137 providing permanent stimulation via the wirelessly connected implanted unit, externally controlled adjustments of stimulation parameters are easily possible.

It should be understood that neuromodulation may inter alia comprise electrical stimulation, neurorecording or recording of other body signals, recording and/or utilizing external and/or behavioral signals all to restore healthy neural functions and/or alleviate neurological disorders and diseases. This list of therapy modalities is not intended to be exhaustive, as developments in this field are so dynamic and other applications may also be possible. The term neuromodulation is to be understood in the context of this disclosure that it relates to stimulation with electrical signals, and further includes (but is not limited to) modulation with pharmacological agents and the like.

Additionally, reduced graphene oxide, as a layered structure or film for the at least one electrode, has shown to be superior in comparison to standard commercially available neural interfaces based on metallic microelectrodes made of platinum Pt, platinum-iridium (Pt/Ir), iridium oxide (IrOx) or titanium nitride (TiN). These metal materials interact with the living tissue through a combination of Faradaic and capacitive currents, offer a limited chemical stability and are rigid. Furthermore, metals performance strongly drops in microelectrodes of tens of micrometres in diameter and metals degrade over continuous tissue stimulation. Reduced graphene oxide instead can be electrochemically activated resulting in an increased capacitance and a lowered impedance. The electrochemical activation is done in an electrolyte solution causing charged ions to permeate into the structure. Thereby, not only the outer surfaces of the structures are electrochemically available and subject to the electrochemical activation, but the interfaces between the layers as well. Consequently, the electrodes to be used can be made even smaller without sacrificing performance.

The reduction of the starting material graphene oxide, which is itself non-conductive, may be carried out by hydrothermal reduction, whereby e.g. the structure or film of graphene oxide is exposed to subcritical water. During this process, the protons from the water react with the oxygen-containing functionalizations of the flakes, partially removing them and opening in-plane holes or pores. Contrary to chemically or just thermally reduction, this process permits the structure to be permeable to aqueous solutions while being electrically conductive. The synthesis of hydrothermally reduced graphene oxide does not involve any hazardous chemical, so the biocompatibility is maintained.

The at least one implant unit may further comprise a housing accommodating the first power receiver (in particular comprising an antenna) and a power processing system (for example comprising a capacitor).

Generally speaking, power transfer and information transfer can be realized via the same antenna. Power transfer and information transfer can be realized by using inductivity and/or ultrasound. If the inductive approach is chose, the regime of frequencies is similar to existing systems. Frequencies can range from approx. 30 kHz up to 13 MHz. Communication, in particular control signals transfers is embedded in the power transmission. It is possible that communication and power transfer is happening and realized at the same time or time multiplexed. When an ultrasound approach is used, this can be realized by using ultrasound transducers to transfer energy and information. For example, chip transducers like CMUTs (Capacitive Micromachined Ultrasonic Transducers) can be used and integrated in several small ways. The used frequencies can range from kHz to MHz ranges.

The implant unit may also comprise rechargeable power source designed for long-term use which is accommodated in the housing as well.

The lead may be connected to the housing by its proximal end, while the electrode array may be arranged at the distal end of the lead. The portion of the lead between distal and proximal end is flexible. It is also conceivable that the electrode array comprises more than one portion which are arranged spaced apart along the lead so that one lead is able to stimulate brain tissue at different sites or areas.

The first antenna may be an omnidirectional antenna so that a wireless connection to the wearable device is possible even if the alignment to each other is not ideal.

The amount, size and pattern of the electrodes arranged in the electrode array may be adapted to the target site or area of the brain tissue.

The parts or components of the implant unit are made of materials which are not prone to wear and are biocompatible as well as not degradable, especially those in direct contact with the tissue. The respective material can be one of the group of titanium, ceramics, glass, biocompatible polymers and/or silicon rubber or any suitable combination of them.

The wearable device comprises control electronics, a power source and the second antenna all accommodated in a housing, and further a form-fitted portion which is anatomically adapted to the area behind the patient's ear.

The implant unit and the wearable device may be electromagnetic compatible, i.e. they are both sufficiently shielded against electromagnetic interference. Furthermore, the directive 2014/30/EU on electromagnetic compatibility, among others, shall be complied with.

The wireless connection between the implant unit and the wearable device can be continuously established or within predetermined intervals.

All possible wireless connections or data exchange pathways may be encrypted to ensure the privacy of sensitive patient data.

In a possible embodiment, the implant unit further comprises a pulse generator.

The pulse generator, comprising electronic components, generates the stimulation pulses which are routed through the lead to the electrode array and further to the respective electrodes. The generation of the stimulation pulses depends on the received control signals sent from the wearable device.

Furthermore, it is possible that the implant unit further comprises a recording system and/or sensing system to acquire signals, especially neurophysiological signals. The signals can be used to improve the provided therapy. In particular, this way a closed or semi-closed loop system can be realized. Also, the data can be used for analysis, especially in connection with the analysis of the therapy and also for the monitoring over the time of the therapy.

In another possible embodiment, the wearable device is rechargeable.

To preserve the integrity of the wearable unit, the power source inside the wearable device is rechargeable, wherein the charging process can either be wired by means of a charging port provided at the wearable unit or wireless, e.g. via inductive charging. In particular, a wireless charging likewise the wireless charging for smartphones or wearables can be used.

In a further possible embodiment, the wearable device is configured to wirelessly charge the at least one implant unit.

If the rechargeable power source of the implant unit reaches or tends to reach its charging capacity, the wearable device wirelessly recharges the implant unit via power beam, i.e. inductive coupling.

The capacity of the power source (e.g. the battery) can be configured such that automatic routines for recharging can be implemented. Such routines could be e.g. recharging every night, for example by having a recharging module in the pillow of the patient. Also, a weekly or calendar-based routine with fixed recharging dates will be helpful for the patient and user of the system.

It may also be provided that the rechargeable power source is charged in predetermined intervals, depending on the kind of rechargeable power source, since a memory effect degrading the power source of the implant unit is to be avoided.

The inductive charging process is dimensioned in such a way that there is no significant heating of the components involved.

In a further possible embodiment, the wearable device is form-fitted to a human ear.

It is possible that the wearable device has a personalized and/or customized form-fit to an ear of a human.

The wearable device comprises a portion form-fitted to the area behind the patient's ear conch, i.e. adapted to the corresponding anatomy. The wearable device thus resembles a behind-the-ear hearing aid in its appearance and fit.

To adapt the wearable device to the patients' needs and to provide an individualization, a personalized sleeve for the patient can be provided. This can be e.g. done with a personalized 3D printed elastomer, e.g. silicon sleeve can be provided.

In a further possible embodiment, the wearable device comprises a device software.

The device software ensures that functionality of the wearable device is updateable and/or upgradable.

The device software can be updated and/or upgraded either wired by means of a data port or by a wirelessly data connection. The data port may be a combined port also serving as the charging port as mentioned before.

In a further possible embodiment, the wearable device is configured to wirelessly exchange data with a mobile device, such as a smartphone, another personal electronic device (such as a laptop or tablet computer), and/or a data base station.

In this respect, the term "data" is used for any value in connection with the neuromodulation system according to the present disclosure. Data can thus be the measured values of the implant unit, the setting parameters for the implant unit or the like.

Consequently, the mobile device can transmit adjusted setting parameters to the implant unit on the basis of the received measured values.

The setting parameters are first transmitted to the wearable device, which then sends or uploads them wirelessly to the implant unit.

Alternatively or additionally, the wearable device can also establish a wireless connection to a data base station. The data base station can be a data cloud or a server station capable to process the received data and to provide data. The data base station may be located at a medical facility so that the clinician in charge can monitor adjust the patient's data remotely.

In a further possible embodiment, the mobile device comprises a software application configured to process data received from the device and/or establish a network data link to the data base station.

The software application evaluates and analyses the received data. Additionally, the software application may be configured to prepare the results graphically to the patient. Furthermore, the software application may determine optimized therapy parameters and present them to the sufficiently instructed patient who then can chose to accept or decline an adjustment of the parameters. The analysis of the received data by means of the software application may be based on artificial intelligence.

Additionally or alternatively, the data analysis may be performed by means of a data base station, for instance, provided with an artificial intelligence.

In a further possible embodiment, the implant unit is wirelessly rechargeable.

As the wearable device is meant to be configured to be capable to wirelessly charge the implant unit, the implant unit itself must consequently be rechargeable. This way, the implant is provided with a power source.

It is possible that there can be an implant embodied without a power source.

The power source is mainly to bridge the gap between replacing or taking off the wearable (sleep, shower) and still be able to provide therapy. If this is not needed for certain therapy, the implant can be embodied as a smaller device without battery.

Generally speaking, the power source shall, in normal operation with wearable attached, power the device (like a cochlear device without battery) and close the loop with external data and sensors, and processing of data.

It is further conceivable that the implant unit comprises two separate rechargeable power sources in the case one of them should be malfunctioning. Thus, the intact power source can maintain the functionality and the patient does not have to undergo any surgery for maintenance reasons of the implant unit.

In a further possible embodiment, the implant unit is anatomically fitted to an implant site and configured to be implanted cranial.

The housing of the implant unit may be flat so that the scalp tissue at the implant site is affected as little as possible. Additionally, the housing may be of a flexible material so that an adaptation to the skull bone can be achieved.

The implant unit according to the present disclosure is implantable fully cranial, as the placement of the pulse generator in the chest region and its connecting are no longer necessary.

The object of the present disclosure can further by solved by a method for neuromodulation, which comprises the following steps:

establishing a first bidirectional wireless connection between an implant unit comprising a pulse generator and a wearable device; and transmitting pulse commands from the wearable device to the implant unit via the first bidirectional wireless connection to cause a stimulation of a target.

The control electronic components can be outsourced to the wearable device, thus reducing the size of the implant and allowing for a flexible adjustment (control) of the therapy parameters.

The established first bidirectional wireless connection between implant unit and wearable device ensures the controllability of the implant unit after implantation and guarantees a reliable data exchange.

In another possible embodiment, the method for neuromodulation further comprises the step of transmitting signals, recorded by the implant unit, from the implant unit to the wearable device via the first bidirectional wireless connection.

The electrodes of the electrode array fulfil two tasks: on the one hand, they lead the stimulation impulse into the brain tissue and, on the other hand, they record brain signals, such as with the resolution of individual nerve cells. The recorded signals are transferred from the electrode to an antenna of the implant unit from where they are transferred to the wearable device. The wearable device then forwards the recorded signals as a data set to a mobile device which I configured to process the data and, in some embodiments, can determine if an adjustment of the therapy parameters is required.

In a further possible embodiment, the method for neuromodulation further comprises a step of wirelessly charging the implant unit by the wearable device via the first bidirectional wireless connection.

The implant unit does not have to be surgically replaced as soon as its power source is depleted. Modern rechargeable power sources are also improved in terms of a memory effect, so that the increased duration of use of the implant unit requires at best only the initial surgical insertion.

Furthermore, the method may comprise the following further steps:
providing at least two implant units;
establishing a bidirectional wireless connection between implant units comprising a pulse generator; and
exchanging information regarding stimulation settings and/or therapy parameters and/or feedback information and/or synchronization of the stimulation pulses.

As described above, there may be two implant units for the two sides of the (human) patient. It is desirable and enhances the overall functionality of the neuromodulation system, if the two implant units are capable to communicate with each other and to exchange at least one of data, signals, parameters, feedback or the like.

Additionally, the method may comprise the following further steps:
providing at least two wearable devices;
establishing a bidirectional wireless connection between wearable devices; and
exchanging information regarding stimulation settings and/or therapy parameters and/or feedback information and/or synchronization of the stimulation pulses.

This way, also the wearables are able to exchange at least one of data, signals, parameters, feedback or the like.

Moreover, it is possible that the method further comprises at least the following steps:

establishing a bidirectional wireless connection between the wearable device, the mobile device and a second wearable device either directly and/or indirectly; and
exchanging information regarding stimulation settings, therapy parameters, feedback information and synchronization of the stimulation pulses.

The disclosure further relates to a use of a neuromodulation system as defined above.

BRIEF DESCRIPTION OF THE FIGURES

Further details of the present disclosure shall now be disclosed in the connection with the drawings.

It is shown in

DETAILED DESCRIPTION

Neural implants offer therapeutic options to patients suffering from certain neurological disorders and other neural impairments (e.g. deafness, Parkinson's disease, amputations, etc.). Such technology currently consists of implantable devices that either electrically record or stimulate the nervous system using millimetre-scale metallic electrodes. To achieve broader acceptance of neural implants as a therapy, there is a need for a step-change improvement to their efficacy so that the therapeutic approach outweighs inter alia the risks from surgical implantation.

Figure 1:
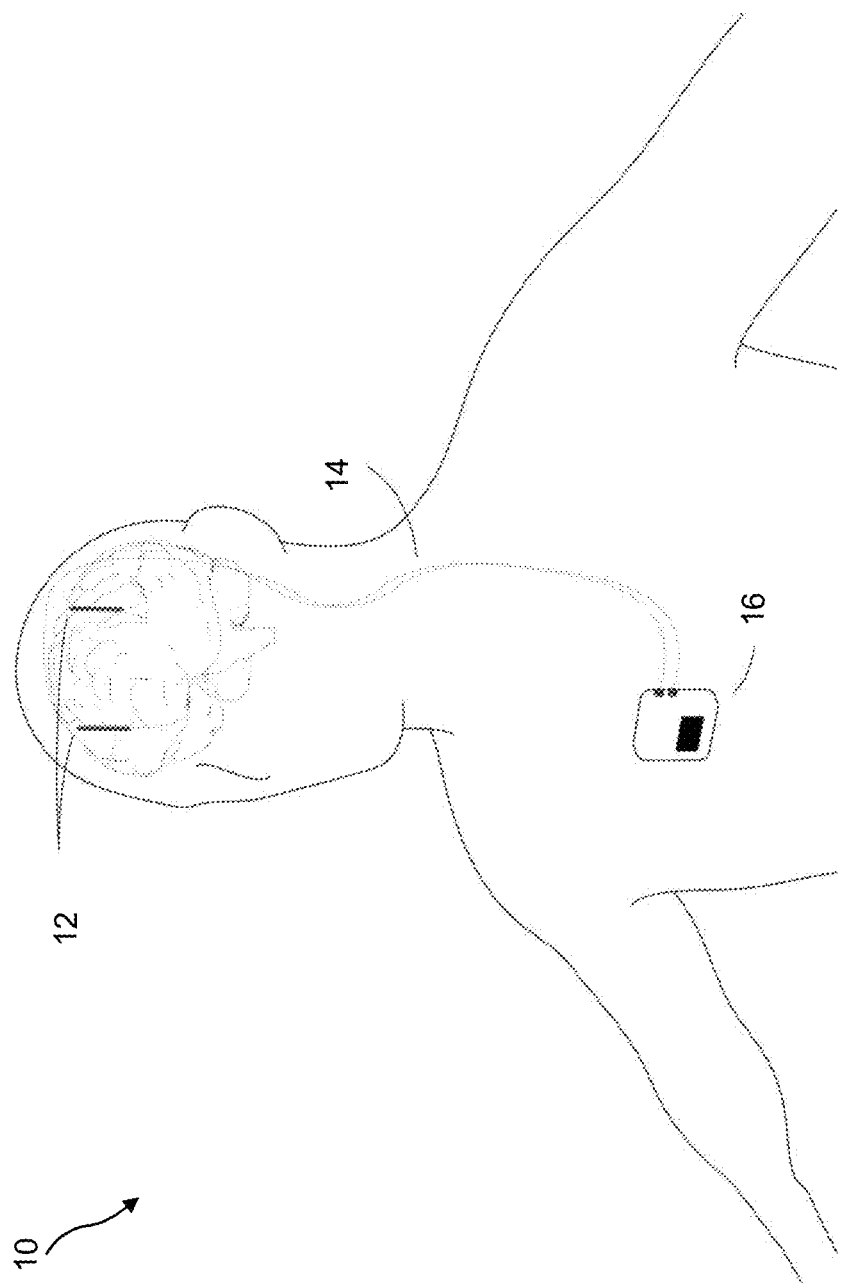
FIG. 1 a prior art neurostimulation system.

FIG. 1 shows a prior art embodiment of a neuromodulation system 10 implanted in a patient.

The embodiment of the neuromodulation system 10 shown in FIG. 1 comprises two leads 12, a pulse generator 16 and one connecting cable 14 per lead 12 to connect the leads 12 separately to the pulse generator 16.

The prior art neuromodulation system 10 needs the pulse generator 16 to be implanted in the patient's chest region, as can be derived from FIG. 1. Consequently, a follow-up surgery after first implantation of the neurostimulation system 10 is required as soon as the battery or power source of the pulse generator 16 tends to reach its end of service life.

Moreover, the connecting cables 14 must be surgically routed from the impulse generator 16 to the leads 12 during the surgical insertion. In this regard, care must be taken that the connecting cables 14 and in particular the connection between the pulse generator 16 and the leads 12 are not affected by the patient's body movements after implantation.

What is more is that generally the settings or parameters of the pulse generator 16 are set once before the implantation and it is not possible to adjust these settings after implantation. This applies in principle to the first-generation pulse generators. Modern implantable pulse generators are adjustable via a wireless connection between the pulse generator 16 and a terminal station. These terminals are often only available in a medical facility, so a patient is forced to visit a respective facility for an adjustment of the settings.

Figure 2:
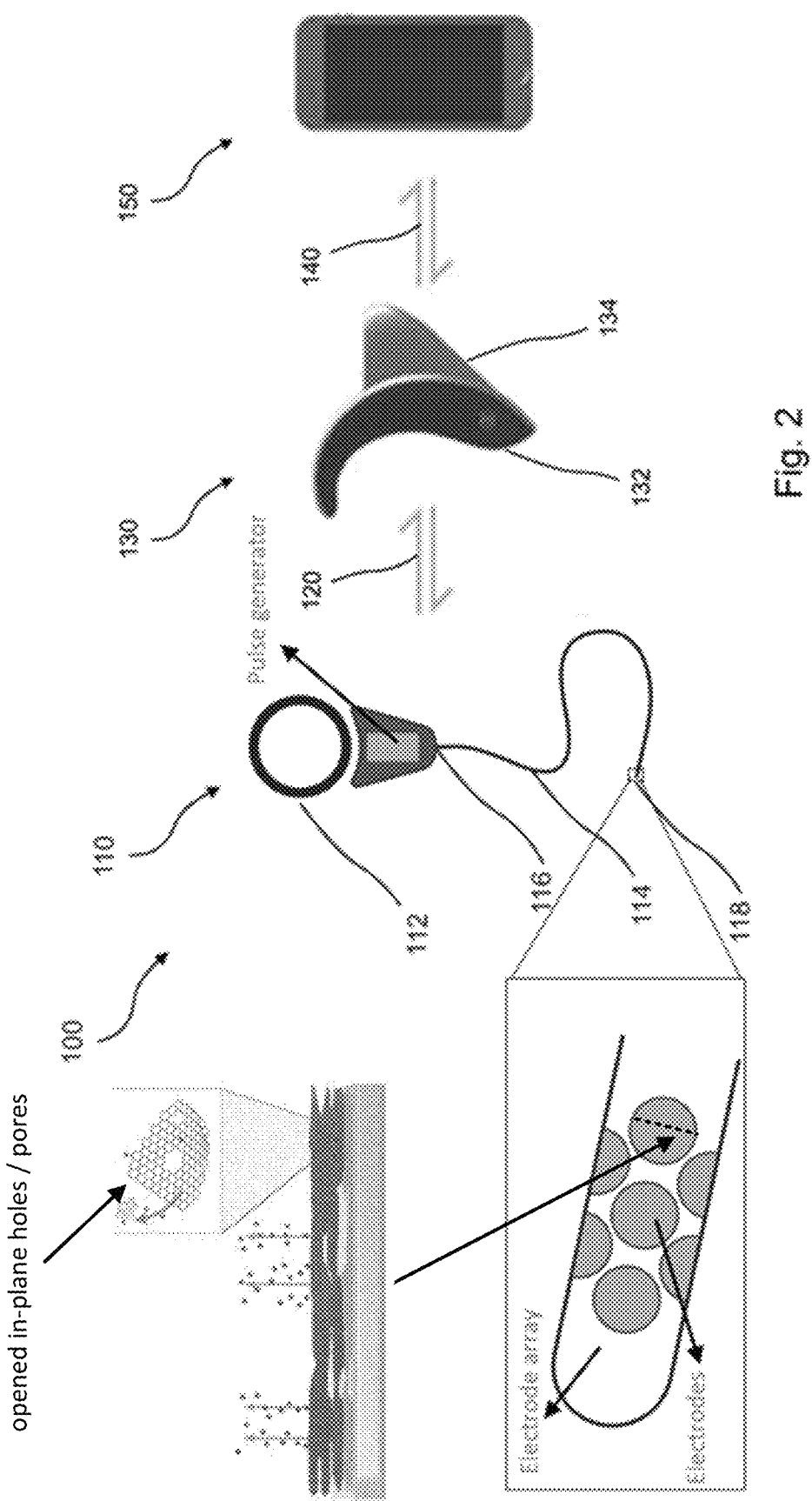
FIG. 2 an embodiment of a neuromodulation system according to the present disclosure.

FIG. 2 shows an embodiment of a neuromodulation system 100 according to the present disclosure comprising an implant unit 110, a wearable device 130, a mobile device 150, such as a smart phone.

The neuromodulation system 100 may further comprise a data base station (not shown).

The implant unit 110 comprises a first antenna 112, a lead 114 and a pulse generator (not shown).

The first antenna 112 may be an omnidirectional antenna.

The lead 114 comprises an electrode array having at least one electrode. The lead 114 has a proximal end 116 and a distal end 118, wherein the electrode array is arranged at the distal end 118 of the lead 114.

The electrodes of the electrode array may be made of graphene, or of a hydrothermally reduced graphene oxide.

The wearable device 130 comprises a portion 132 adapted or form-fitted to the anatomy of a patient's ear and a housing 134.

The portion 132 may be made of a sufficiently flexible and adaptable material.

In particular, the core of the portion 132 may have a fixed shape.

This shape will anatomically align with the position of the implant on the body. It is possible to add a sleeve of for example silicon rubber or another soft material to optimize the comfort of wearing the device and/or fixate the position better (e.g. movement and position relative to the antenna and/or prevent detachment during daily life activities).

The housing 134 accommodates inter alia a rechargeable power source, control electronics unit and a second antenna 135.

The control electronic unit comprises a device software which is updatable either via a wireless connection or a port provided at the wearable device 130.

The implant unit 110 and the wearable device 130 are wirelessly connected via the first bidirectional wireless connection 120. By means of this first wireless bidirectional connection 120 control signals or commands and measured values or recorded data can be exchanged as well as power beaming, i.e. inductive coupling to charge the implant unit 110, can be conducted.

Furthermore, instead (or additionally) of an inductive coupling also ultrasound can be used to transfer and/or receive power and/or control signals and/or communication signals.

In case that wearable devices are on both sides of the head of the patient (i.e. on the left and right side), then the devices shall be able to communicate with each other. In particular, it can be realized such that there is one IPG serving for both wearable devices, and so both leads will be controlled via one IPG and via the two wearable devices. The connection can be e.g. established by using Bluetooth or NFMI (Near Field Magnetic Induction communication) or indirectly via a mobile phone, which can be a hub and coupling element.

In particular, there can be two implant units 110. A bidirectional wireless connection between implant units 110 can be established. This setup of the system is then capable to exchange information regarding stimulation settings and/or therapy parameters and/or feedback information and/or synchronization of the stimulation pulses.

Also, two wearable devices 130 can be provided. A bidirectional wireless connection between the wearable devices 130 can be established and provided. This setup of the system is capable to exchange information regarding stimulation settings and/or therapy parameters and/or feedback information and/or synchronization of the stimulation pulses.

The system can be further be capable to establish a bidirectional wireless connection between the wearable device 130, the mobile device 150 and a second wearable device 130 either directly and/or indirectly and is configured to exchange information regarding stimulation settings, therapy parameters, feedback information and synchronization of the stimulation pulses.

This way a semi-closed loop system or even a closed loop system can be established.

For reasons of setup or data processing the wearable device can further be wirelessly connected to the mobile device 150 via a second wireless bidirectional connection 140.

The second bidirectional wireless connection may be one of the group of: a 3G/4G/5G (or further generations) wireless, a WIFI network connection, a near field connection and a Bluetooth connection.

The mobile device 150 comprises a software application to process the data received from the wearable device 130 and/or to display the data.

Furthermore, it is possible to adjust the settings or parameters of the neuromodulation therapy by means of the software application. The new settings are forwarded from the mobile device 150 to the wearable device 130 via the second wireless bidirectional connection 140.

Alternatively or additionally, the mobile device 150 can establish a link to the data base station to exchange measured data of the patient or to receive optimized settings for the therapy. By forwarding the data to a data base station which may be located at a medical facility the responsible clinician can monitor the therapy without the patient having to present.

The wearable device 150 may additionally be configured to establish an individual wireless connection to the data base as a matter of redundancy.

Figure 3:
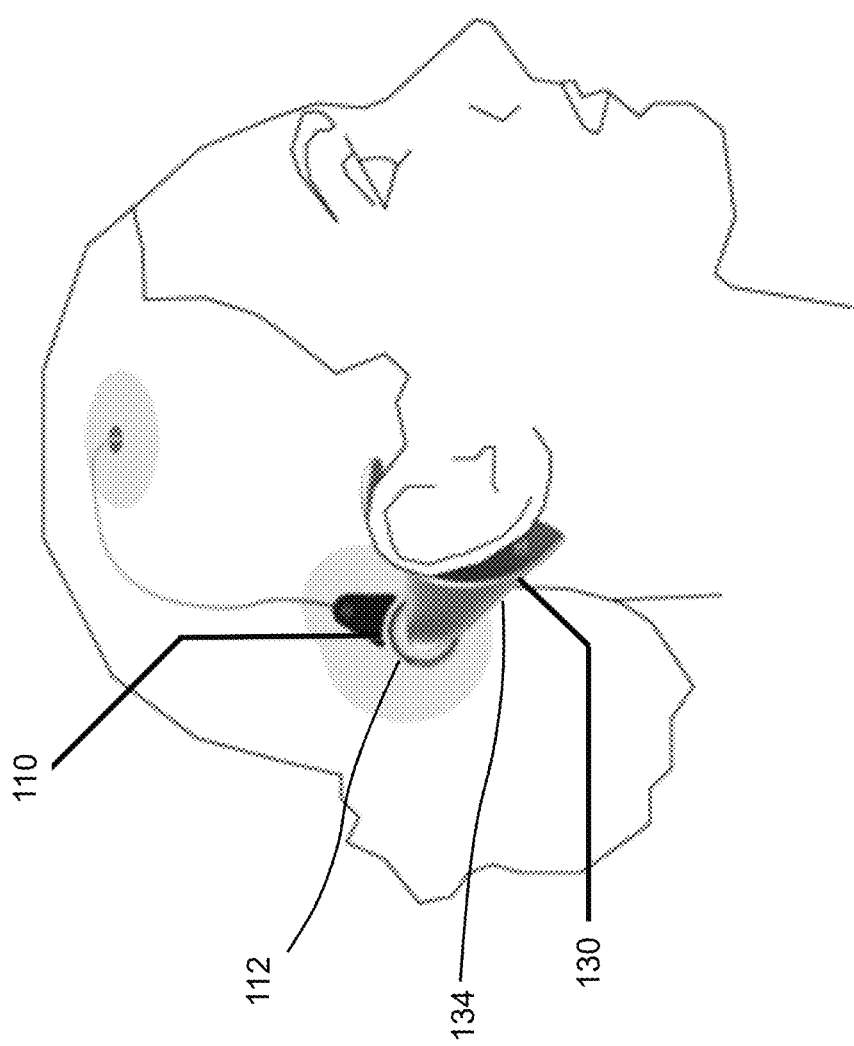
FIG. 3 the neuromodulation system of FIG. 2 attached and worn by a patient.

In FIG. 3, the implant unit 110 of FIG. 1 is presented implanted in a patient's head. The first antenna 112 of the implant unit 110 is located under the scalp behind one ear, while the distal end 118 of the lead 114 reaches through the patient's cranium so that the electrode array can be brought into contact with the brain tissue.

The wearable device 130 is positioned behind the corresponding patient's ear, wherein the second antenna accommodated in the housing 134 of the wearable device 130 and the first antenna 112 of the implant unit 110 are aligned to each other.

It is possible that a patient is equipped with a combination of an implant unit 110 and a wearable device 130 at each ear so that two electrode arrays are stimulating and/or recording at the different target sites of the brain tissue.

It is also possible that one wearable device 130 controls two implanted implant units 110. In this regard, the wearable device may e.g. either comprise an additional antenna or the antennas 112 of the implant units 110 are controlled with different frequencies.

REFERENCE SIGNS 10 prior art neurostimulation system
12 leads
14 connecting cables
16 pulse generator
100 neuromodulation system
110 implant unit
112 first antenna
114 lead
116 proximal end of the lead
118 distal end of the lead
120 first bidirectional wireless connection
130 wearable device
132 form-fitted portion
134 housing
140 second bidirectional wireless connection
150 mobile device

The invention claimed is:

1. A neuromodulation system, in particular for Cortical and/or Deep Brain Stimulation and/or Modulation, comprising:
at least one implant unit comprising:
at least one first antenna, and
at least one lead having at least one electrode array with at least one electrode; and
at least one wearable device comprising at least one second antenna,
wherein the at least one wearable device is configured to wirelessly control and wirelessly communicate with the at least one implant unit,
wherein the at least one electrode is made of hydrothermally reduced graphene oxide, which is activated causing charged ions to permeate into the structure of the hydrothermally reduced graphene oxide, and
wherein the hydrothermally reduced graphene oxide is electrochemically activated in an electrolyte solution.

2. The neuromodulation system according to claim 1, wherein
the at least one implant unit further comprises a pulse generator.

3. The neuromodulation system according to claim 1, wherein
the at least one implant unit further comprises a recording system and/or sensing system to acquire signals, especially neurophysiological signals.

4. The neuromodulation system according to claim 3, wherein
the at least one wearable device is rechargeable.

5. The neuromodulation system according to claim 3, wherein
the at least one wearable device is configured to wirelessly charge or power the at least one implant unit.

6. The neuromodulation system according to claim 3, wherein
the at least one wearable device is form-fitted to a human ear.

7. The neuromodulation system according to claim 3, wherein
the at least one wearable device has a portion form-fitted to the anatomy of a patient's ear.

8. The neuromodulation system according to claim 3, wherein
the at least one wearable device comprises a device software.

9. The neuromodulation system according to claim 3, wherein
the at least one wearable device is configured to wirelessly exchange data with a mobile device and/or a data base station.

10. The neuromodulation system according to claim 9, wherein
the mobile device comprises a software application configured to process data received from the at least one wearable device and/or establish a network data link to the data base station.

11. The neuromodulation system according to claim 3, wherein
the at least one implant unit is wirelessly rechargeable.

12. The neuromodulation system according to claim 3, wherein
the at least one implant unit is anatomically fitted to an implant site and configured to be implanted cranially.

13. The neuromodulation system according to claim 1, wherein the hydrothermally reduced graphene oxide includes opened in-plane holes or pores.

14. The neuromodulation system according to claim 1, wherein the at least one implant unit includes one or more wireless connections or data exchange pathways; and wherein all of the one or more wireless connections or data exchange pathways are encrypted.

15. The neuromodulation system according to claim 1, wherein the at least one implant unit is head-implanted.

16. The neuromodulation system according to claim 1, wherein the at least one second antenna is integrated into the at least one wearable device.

17. The neuromodulation system according to claim 1, wherein the at least one wearable device further includes a power transfer unit providing stimulation via the at least one implant unit.

18. A method for neurostimulation, which comprises the following steps:
providing a first implant unit, a second implant unit, and a wearable device, wherein each of the first implant unit and the second implant unit comprises a pulse generator, and wherein an antenna is positioned within a housing of the wearable device;
establishing a first bidirectional wireless connection between the first implant unit and the wearable device via the antenna;
transmitting pulse commands from the wearable device to the first implant unit via the first bidirectional wireless connection to cause a stimulation of a target;
establishing a second bidirectional wireless connection directly between the first implant unit and the second implant unit; and
exchanging information regarding stimulation settings and/or therapy parameters and/or feedback information and/or synchronization of stimulation pulses via the second bidirectional wireless connection,
wherein the wearable device further includes a power transfer unit providing stimulation via the first implant unit; and
wherein at least one of the first implant unit and the second implant unit comprises at least one lead having at least one electrode array with at least one electrode;
wherein the at least one electrode is made of hydrothermally reduced graphene oxide, which is activated causing charged ions to permeate into the structure of the hydrothermally reduced graphene oxide, and
wherein the hydrothermally reduced graphene oxide is electrochemically activated in an electrolyte solution.

19. The method for neurostimulation according to claim 18, further comprising a step of transmitting signals, recorded by the first implant unit, from the first implant unit to the wearable device via the first bidirectional wireless connection.

20. The method for neurostimulation according to claim 18, further comprising a step of wirelessly charging the first implant unit by the wearable device via the first bidirectional wireless connection.

21. The method for neurostimulation according to claim 18, wherein the wearable device is a first wearable device, further comprising at least the following steps:
providing a second wearable device;
establishing an additional bidirectional wireless connection between the first wearable device and the second wearable device; and
exchanging information regarding stimulation settings and/or therapy parameters and/or feedback information and/or synchronization of stimulation pulses via the additional bidirectional wireless connection.

22. The method for neurostimulation according to claim 18, wherein the wearable device is a first wearable device, further comprising at least the following steps:
establishing an additional bidirectional wireless connection between the first wearable device, a mobile device and a second wearable device either directly and/or indirectly; and
exchanging information regarding stimulation settings, therapy parameters, feedback information and synchronization of stimulation pulses via the additional bidirectional wireless connection.

* * * * *